US012605084B2

(12) United States Patent
Märtens et al.

(10) Patent No.: US 12,605,084 B2
(45) Date of Patent: Apr. 21, 2026

(54) IMPEDANCE CARDIOGRAPHY DEVICE

(71) Applicant: Tallinn University of Technology, Tallinn (EE)

(72) Inventors: Olev Märtens, Tallinn (EE); Anar Abdullayev, Tallinn (EE); Margus Metshein, Tallinn (EE); Antoine Gautier, Lille Cedex (FR); Antoine Frappe, Lille Cedex (FR); Andrei Krivošei, Tallinn (EE); Marek Rist, Tallinn (EE); Paul Annus, Tallinn (EE); Benoit Larras, Lille Cedex (FR); Deepu John, Belfield (IE); Barry Cardiff, Dublin (IE)

(73) Assignee: Tallinn University of Technology, Tallinn (EE)

( * ) Notice: Subject to any disclaimer, the term of this patent is extended or adjusted under 35 U.S.C. 154(b) by 496 days.

(21) Appl. No.: 18/190,622

(22) Filed: Mar. 27, 2023

(65) Prior Publication Data

US 2023/0320606 A1 Oct. 12, 2023

(30) Foreign Application Priority Data

Mar. 29, 2022 (EE) .................................. 202200004

(51) Int. Cl.
| | |
|---|---|
| *A61B 5/029* | (2006.01) |
| *A61B 5/0265* | (2006.01) |
| *A61B 5/053* | (2021.01) |

(52) U.S. Cl.
CPC ............ *A61B 5/0265* (2013.01); *A61B 5/029* (2013.01); *A61B 5/053* (2013.01)

(58) Field of Classification Search
CPC ..... A61B 5/7275; A61B 5/7225; A61B 5/318; A61B 5/7264; A61B 5/7282; A61B 5/053; A61B 5/316; A61B 5/0245; A61B 5/308; A61B 5/30; A61B 5/24; A61B 5/486; A61B 5/05; A61B 5/25; A61B 5/28; A61B 5/346; A61B 5/02; A61B 5/7235; A61B 5/7228; A61B 6/5217; A61N 1/025; A61N 1/00
See application file for complete search history.

(56) References Cited

U.S. PATENT DOCUMENTS

| | | | | | |
|---|---|---|---|---|---|
| 4,289,142 | A | * | 9/1981 | Kearns | ................... A61B 6/541 |
| | | | | | 600/536 |
| 4,450,527 | A | | 5/1984 | Sramek | |

OTHER PUBLICATIONS

A. Gautier et al., "Embedded ICG-based Stroke Volume Measurement System: Comparison of Discrete-Time and 20 Continuous-Time Architectures", retrieved from <hal.archives-ouvertes.fr/hal-03482323> on Mar. 22, 2023.

(Continued)

*Primary Examiner* — Deborah L Malamud
(74) *Attorney, Agent, or Firm* — Meunier Carlin & Curfman LLC

(57) ABSTRACT

The impedance cardiography device comprises an impedance measuring unit, connected to the human body to be measured, a differentiator, a comparator and a microcontroller integrated with an analog-to-digital converter, characterized by that the device further comprises two peak voltage detection units with different polarities (positive and negative), the strobing outputs of them being connected to the digital (binary) inputs of the microcontroller and the analog hold outputs to the inputs of the analog-to-digital converter.

8 Claims, 10 Drawing Sheets

(56)  References Cited

OTHER PUBLICATIONS

Yazdanian H. et al., Design and Implementation of a Portable Impedance Cardiography System for Noninvasive Stroke Volume Monitoring. Journal of Medical Sign & Sensors 2016;6:47-56.

* cited by examiner

IMPEDANCE CARDIOGRAPHY DEVICE

PRIORITY

This application claims priority to Estonian patent application number P202200004 filed on Mar. 29, 2022.

TECHNICAL FIELD

The invention belongs to the field of the measurement technology in healthcare, more precisely to the field of assessment and diagnostics of the work of the heart. The important uses of the invention are medical and daily health monitoring and diagnostics, to receive warnings of cardiac disorders as early as possible.

BACKGROUND OF THE INVENTION

There are known impedance cardiography (ICG) solutions, where the electrical bioimpedance signal (acquired, for example, from the patient's chest or wrist) is digitized with a relatively high resolution and sampling frequency (e.g. with a 16-bit analog-to-digital converter with a frequency of 200 samples per second) and the resulting digitized waveform is further analyzed with special software in a local microprocessor (U.S. Pat. No. 4,450,527) or in an embedded system (A. Gautier et al., "Embedded ICG-based Stroke Volume Measurement System: Comparison of Discrete-Time and Continuous-Time Architectures", hal.archives-ouvertes.fr/hal-03482323) or sent (e.g. via wireless connection) to a computer or similar device for analysis (e.g. H. Yazdanian et al., 2016, "Design and Implementation of a Portable Impedance Cardiography System for Noninvasive Stroke Volume Monitoring", Journ. of Medical Signals and Sensors. 6, pp. 47-56).

Such solutions have several disadvantages:
1) the external computer as part of the system cannot be the basis of autonomous (with event detection with local intelligence) or small-sized and low-energy devices;
2) to determine the characteristic points (B, C, X) of the heart cycle (see the mentioned H. Yazdanian et al.), the local digital processor includes sophisticated analysis and calculations over a relatively large number of samples of the signal, which makes it impossible to implement the device as a very small-size low-power and low-cost chips and wearables;
3) known solutions have also an important drawback—the high-resolution and high-sampling frequency analog-to-digital converters have sophisticated schematics and high energy consumption;
4) while reducing the sampling frequency or the resolution of the analog-to-digital converter (ADC) in order to achieve lower power consumption, the accuracy of the measurement of ICG values, both in time and amplitude domains, while determining the characteristic points of ICG cycles and, consequently, also in the further estimation of ICG parameters, is significantly reduced. Known impedance cardiography device solution is described in U.S. Pat. No. 4,450,527 (B. Sramek, "Non-invasive continuous cardio monitor"), where the first differentiator finds the derivative (dZ/dt) of the bioimpedance (Z) result measured from a person (eg from the chest) as the impedance cardiography (ICG) signal. And to find the ICG characteristic points (B, C, X) (where C and X are the maximum and minimum of dZ/dt during one period of cardiac cycle), this solution contains a second differentiator for taking the derivative and a comparator at its output to fix the zero crossings of the second derivative. From the B, C, X value of each heart cycle, hemodynamic parameters such as LVET (left ventricular ejection time), CO (cardiac output), SV (heart stroke volume) and others can be calculated.

The disadvantage of this solution is the use of two cascaded differentiators in the solution, increasing significantly the noise and disturbances of the signal. Differentiation (taking the derivative) as a function is known to be sensitive to small rapid changes, and the double derivative even more.

SUMMARY OF THE INVENTION

The aim of the invention is an improved ICG device for more accurate assessment of ICG parameters by more accurate determination of ICG characteristic points from the ICG waveform, using relatively simple and energy-efficient hardware.

This goal is achieved by a technical solution (FIG. 3), where compared to the known solution, which includes an impedance measurement unit 2, a differentiator 3, a comparator 5 and an analog-to-digital converter 61 integrated with the microcontroller 6, human body 1 to be measured, by the impedance measurement unit 2, output of which is connected to the input of the differentiator 3, the output of which is in turn connected to the input of the analog-to-digital converter 61 integrated with the microcontroller 6 and through the first input of the comparator 5 to the first binary input of the microcontroller 6, wherein the device includes a positive peak value detection unit 4 and a negative peak value detection unit 7, whose inputs are connected to the output of the differentiator 3 and whose binary outputs are connected to the respectively to the second and third binary inputs of the microcontroller 6.

As a rule, the microcontroller 6 needs a clock generator 8.

It can be reasonable (FIG. 4) that the mentioned positive peak value detection unit 4 is, in addition to detecting the peak value event with corresponding strobing pulses, has also means of holding the corresponding analog peak values (until the next ICG signal peak), wherein the analog output of the corresponding positive peak value detection and hold unit 41 is connected to the corresponding input of the analog-to-digital converter 61, integrated with the microcontroller 6.

It may be reasonable (FIG. 5) that the comparator 5 has a second input to which the analog voltage from the hold output of the positive peak value detection and hold unit 41 for detecting and holding the positive peak value mentioned—is given through the voltage divider 9. In that case, it can be reasonable that the transfer coefficient of the mentioned voltage divider 9 is from about 0.1 to 0.20, preferably around 0.15.

Alternatively, it may be reasonable (FIG. 6) that the comparator 5 has a second input to which voltage is supplied from the digital-to-analog converter 62, integrated with the microcontroller 6.

It can also be reasonable (FIG. 7), that in addition to the mentioned positive peak value detection unit 4, the mentioned negative peak value detection unit 71 has also means to hold the corresponding negative analog peak value (until the next ICG signal peak), while the output of this negative analog peak value unit is connected to a separate input of the analog-to-digital converter 61 integrated with the microcontroller 6.

It can be reasonable (FIG. 8) that the mentioned positive peak value detection unit 4, positive peak value detection and hold unit 41, negative peak value detection unit 7 and negative peak value detection and hold unit 71 consist of an operational amplifier, a comparator, of a diode, a capacitor and a resistor, while the non-inverting input of the operational amplifier is connected to the input of the given unit, the output through the semiconductor diode to the inverting input of the same operational amplifier, which in turn is connected to ground through the parallel connection of the resistor and capacitor, and the first input of the comparator is connected to one terminal of the diode, and the second input to the second terminal of the diode, and the output of the comparator is the output of the peak value detection unit. The peak value hold output of the peak value detection unit is connected to the inverting input of the operational amplifier.

BRIEF DESCRIPTION OF THE DRAWINGS

The invention is illustrated by the following figures.

EXAMPLES OF IMPLEMENTATION OF THE INVENTION

Figure 3:
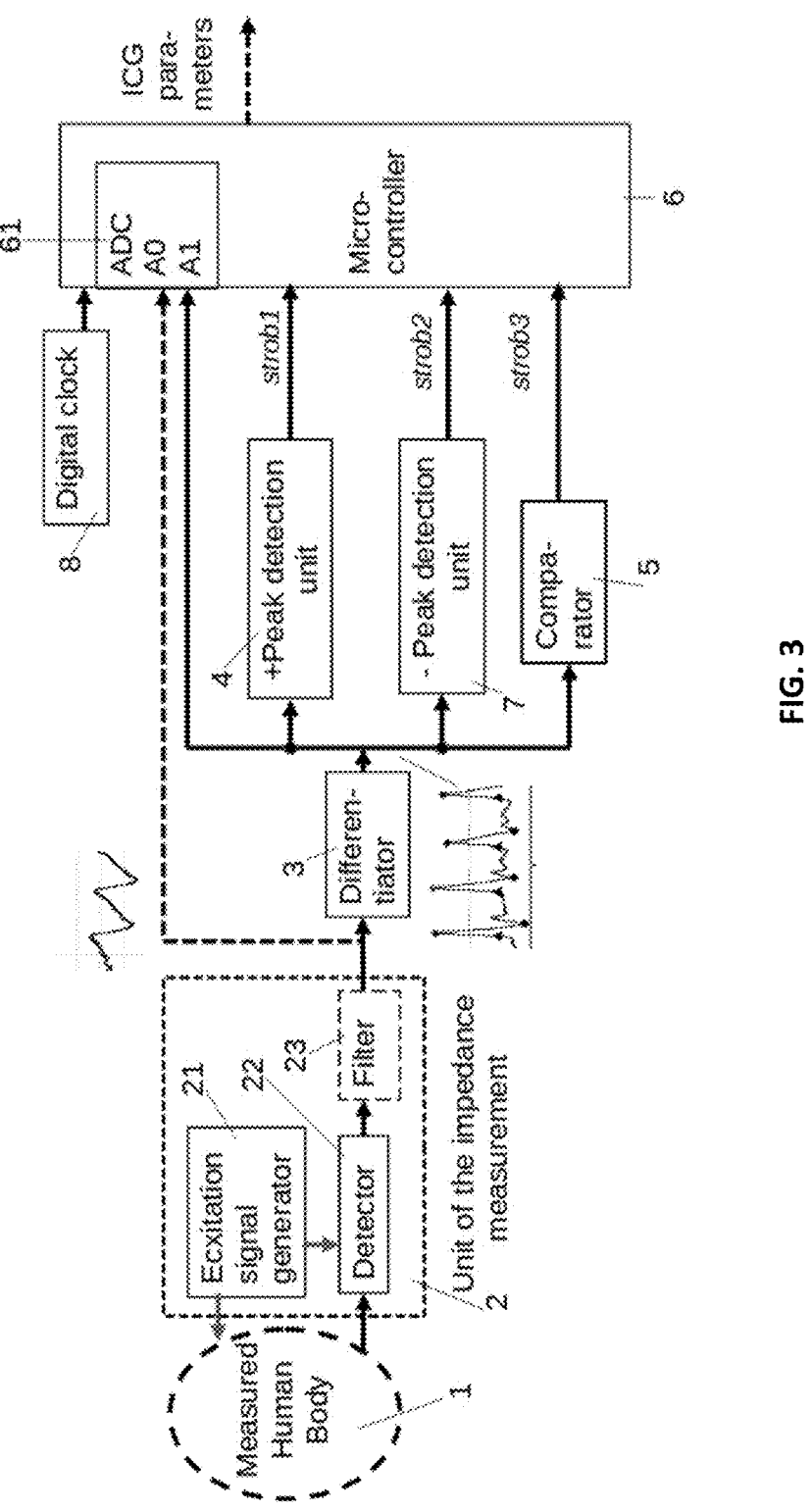
FIG. 3 shows the circuit diagram of the device according to the invention, where the positive peak value detection unit 4 and the negative peak value detection unit 7 have only a binary (strobing) outputs connected to the microcontroller.
Figure 9:
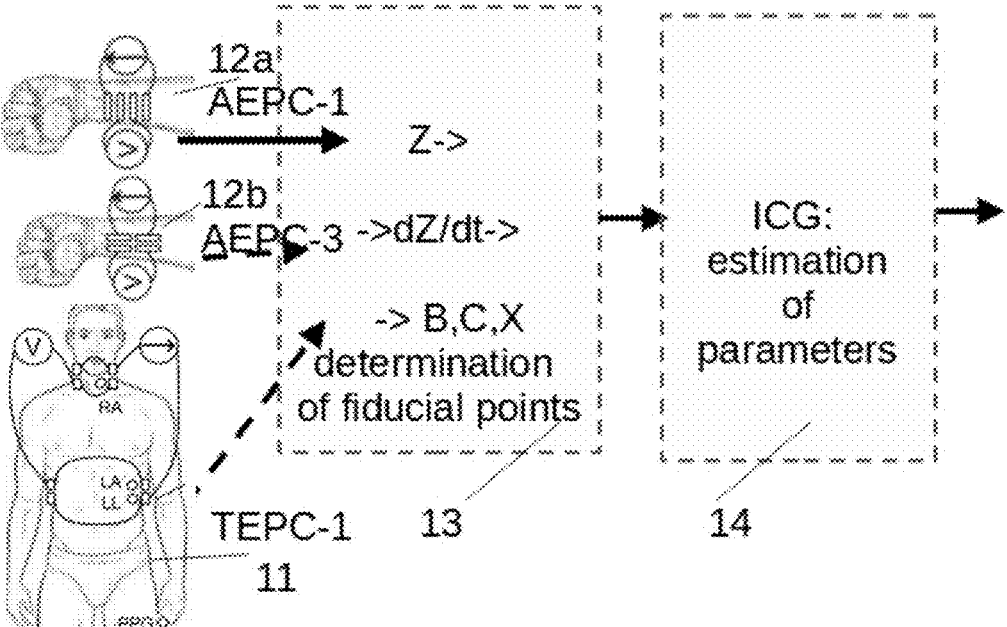
FIG. 9 shows the measurement configurations for ICG signal acquisition. TEPC 11 represents examples of signal measurement from chest and AEPC 12a, 12b from the wrist, and units 13 and 14 are for determining ICG fiducial points and calculating the estimated ICG parameters.

The device is connected to a human body 1, for example by electrodes on the chest 11 or on the wrist 12a, 12b (see FIG. 9). The device (FIG. 3) comprises an impedance measurement unit 2 which typically comprises, for example, a sinusoidal excitation signal generator 21 that generates an excitation signal for measurement, and a detector 22 that demodulates the response signal from the body 1. Preferably, a synchronous detector is used to demodulate the response signal. It is also reasonable to use a low-pass or band-pass filter 23 in the impedance measurement unit at the output of the signal detector, both for suppressing the ripple that occurs during demodulation and interference and artifacts.

Figure 1:
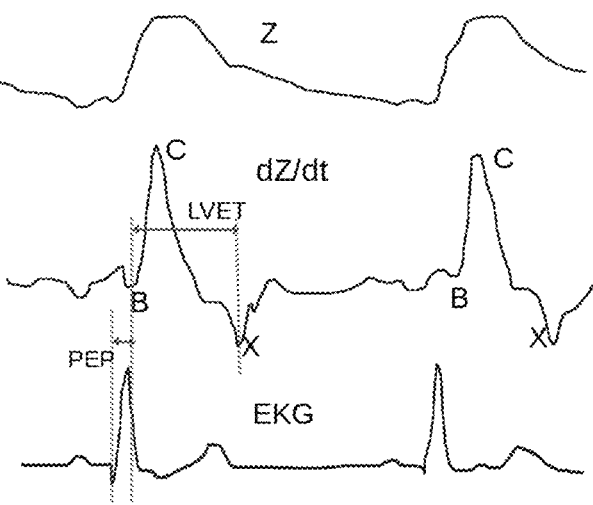
FIG. 1 shows the ICG waveform of one cardiac cycle (see e.g. H. Yazdanian et al.)—the upper curve shows the electrical bioimpedance waveform (Z) signal, the middle—ICG signal (the first derivative of the impedance signal dZ/dt) and the lower curve the ECG (electrocardiography) waveform as for background information.
Figure 2:
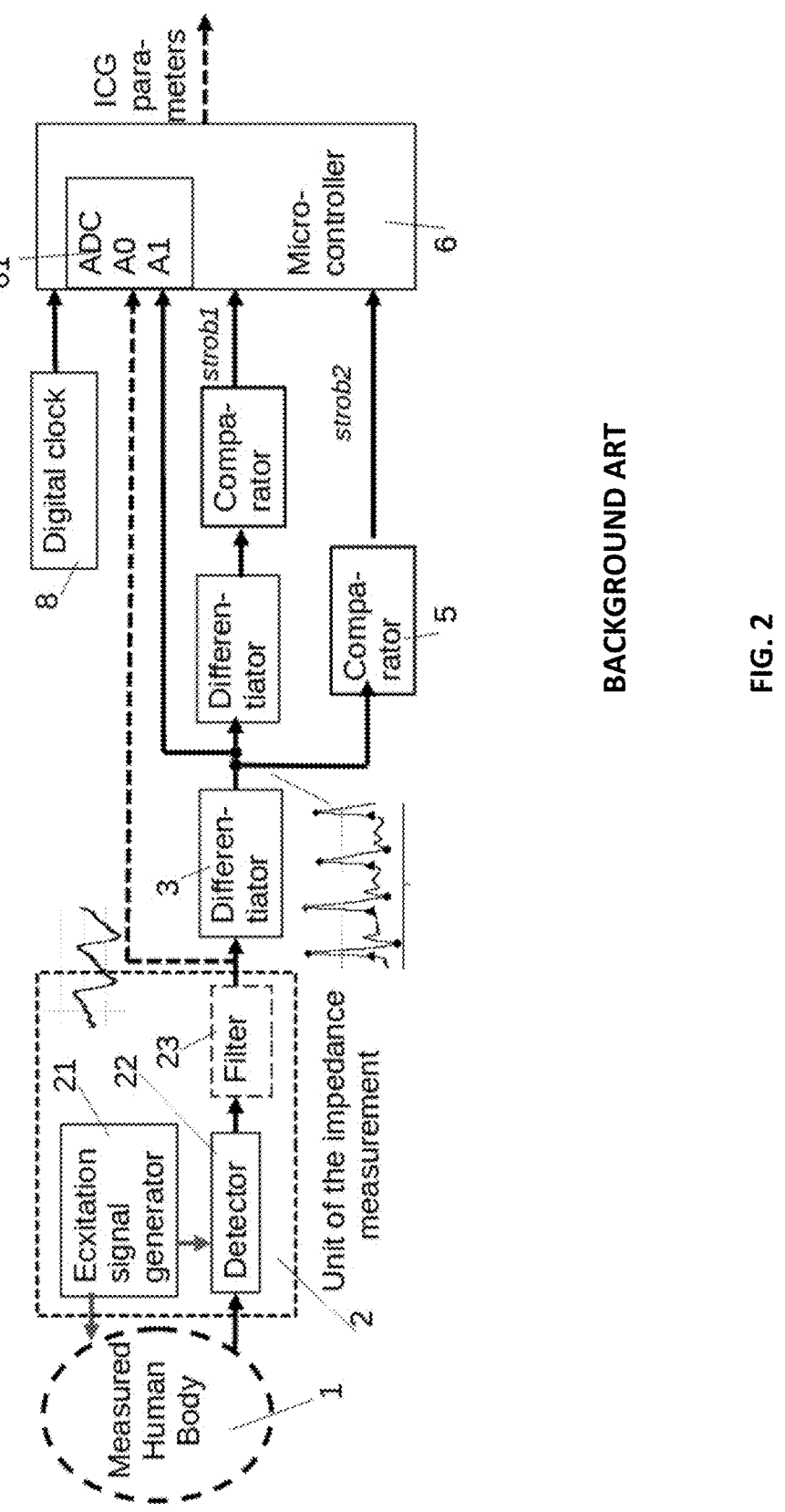
FIG. 2 shows the circuit diagram of the known solution (U.S. Pat. No. 4,450,527).

The detected and filtered impedance (Z) signal passes through the differentiator 3, where the derivative of the impedance signal, ie the ICG signal (dZ/dt), is found. Important points B, C, X (FIG. 1) in each heart cycle are determined in the dZ/dt signal in the simplest case as follows:

C is the maximum (peak value) of the dZ/dt signal in the period;

B is the last zero crossing of the dZ/dt signal before point C;

X is the minimum value (peak value) between two C points.

To calculate the important parameters of the heart's work, such as CO and SV, it is necessary to know the time values and amplitudes of these three points, first of all the interval between the B and X points (LVET) and the amplitude of the C point.

In the proposed solution (according to FIG. 3), the corresponding time instances are found as follows:

In order to find the C-point, there is a positive polarity peak value detection unit 4 which fixes the corresponding time moment (eg as the corresponding reading of the internal counter of the microcontroller) by using the strobing pulse, by means of which the microcontroller 6 (eg by using the interrupt function) and the ADC 61 integrated with the microcontroller 6 fixes and converts the current dZ/dt value to the corresponding numerical value of the signal;

in order to find point B in the diagram, there is a comparator 5, which, when dZ/dt passes zero, generates a strobing pulse of the corresponding moment of time, by means of which the microcontroller 6 (eg using the interrupt function) fixes the corresponding moment of time (eg as a corresponding reading of the internal counter of the microcontroller); if several time values of a possible B point are fixed in the microcontroller between two C points, the last fixed value before the next C point is selected (that is, before the next C point, each possible time value of the B point overwrites the previous value);

In order to find the X-point, there is a negative polarity peak value detection unit 7, which fixes the corresponding time instant (e.g. as the corresponding reading of the internal counter of the microcontroller 6) by using the strobing pulse, by means of which the microcontroller 6 (eg using the interrupt function) fixes and converts the current dZ/dt to the numerical value corresponding to the X-point of the signal.

Figure 4:
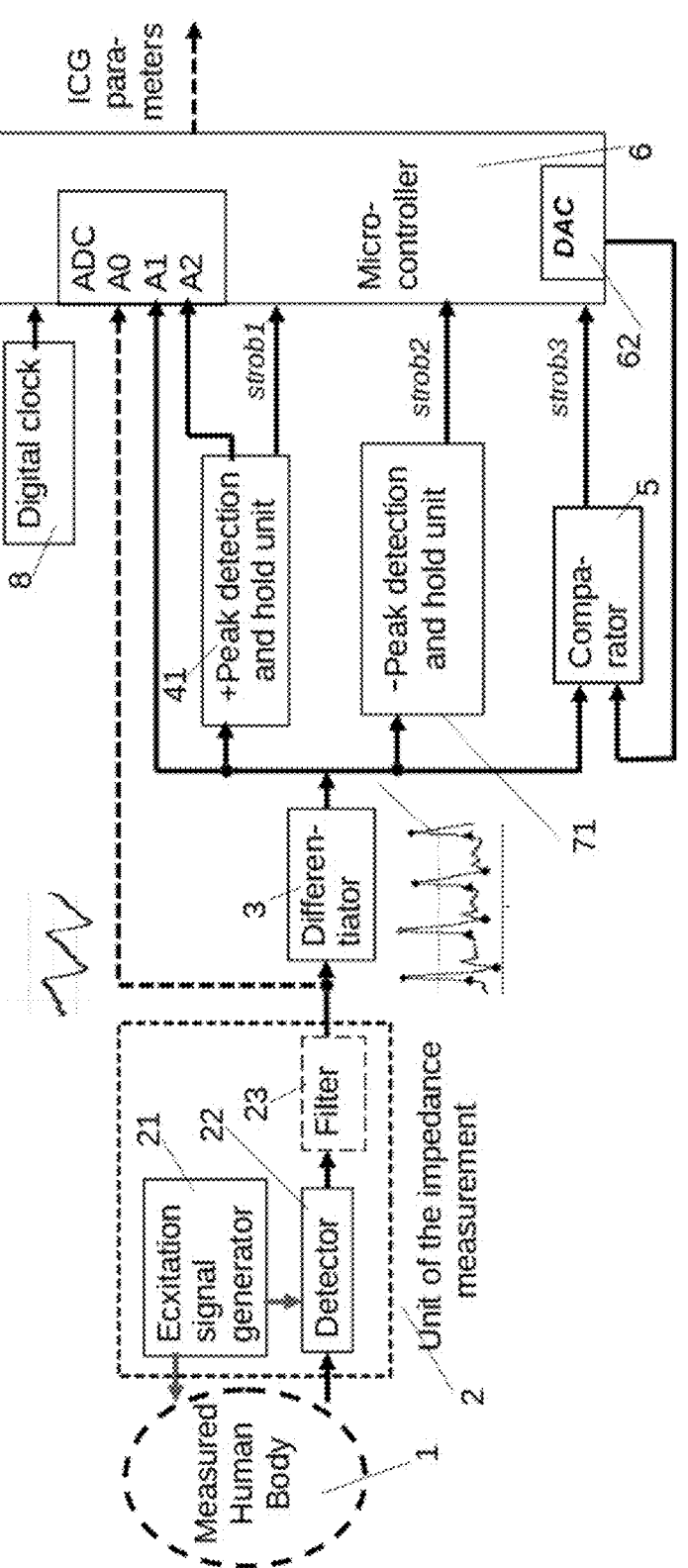
FIG. 4 shows the circuit diagram of the device according to the invention, where the positive peak value detection and hold unit 41 has, in addition to the binary (strobing) output, also an analog peak value hold output, which is connected to the corresponding input of the analog-to-digital converter integrated with the microcontroller.

The proposed solution according to FIG. 4 differs from the previously described solution in that the positive polarity peak value detection unit 4 (for determining the timing and value of point C) includes also the functionality of fixing the corresponding analog peak value itself and transmits the fixed (hold) value to a separate input of the analog-to-digital converter. Such a solution allows to use significantly slower ADC 61, since the positive peak value detection and hold unit 41 operates in this case as a voltage hold unit. The schematic solution of the possible peak value detection and hold unit 41 is shown in FIG. 8.

Figure 5:
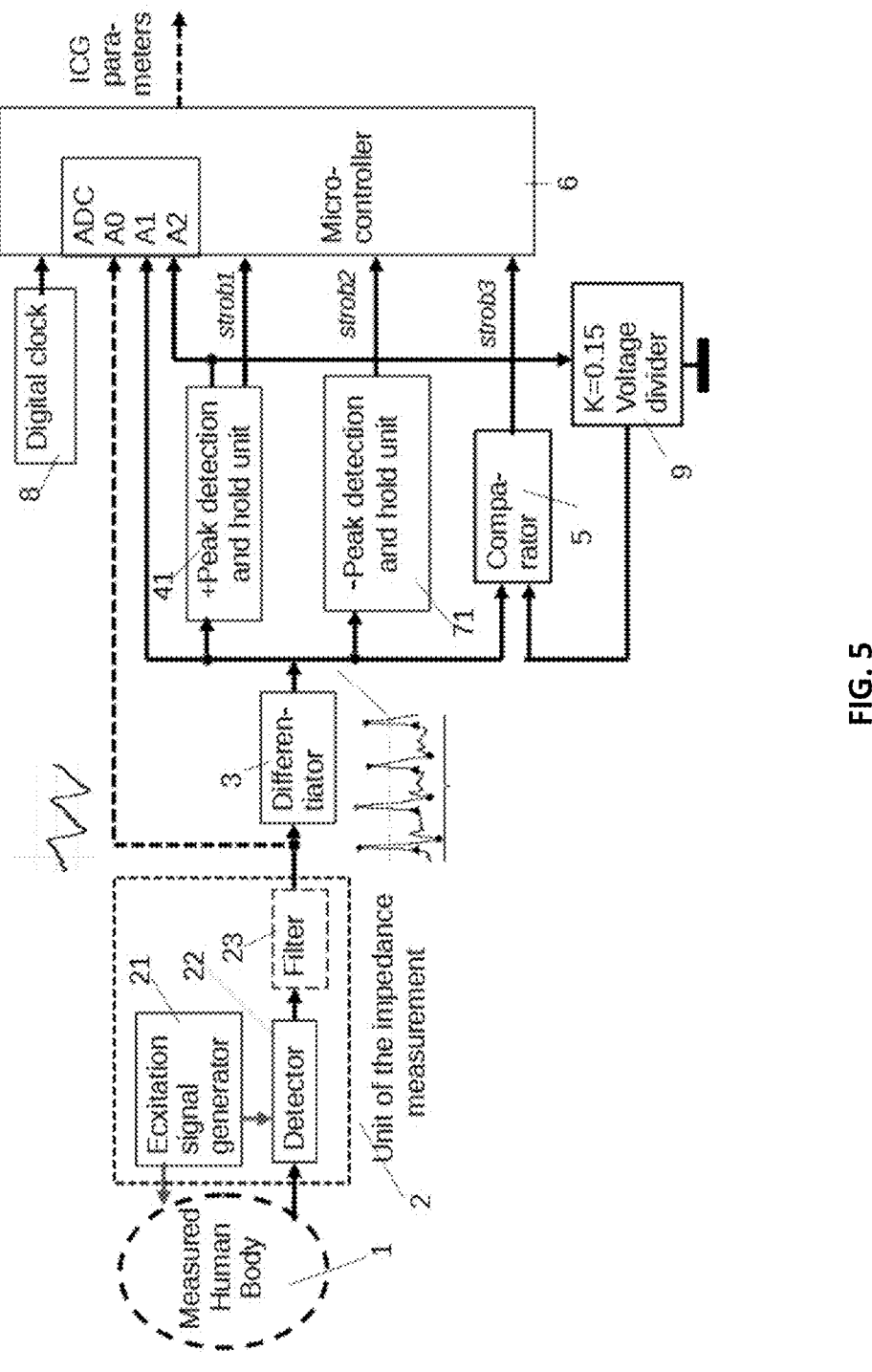
FIG. 5 shows the basic diagram of the device according to the invention, where the signal from the output of the unit 41 for detecting and holding the positive peak value is taken through the voltage divider 9 (with a transmission factor of 0.15) to the second input of the comparator.
Figure 6:
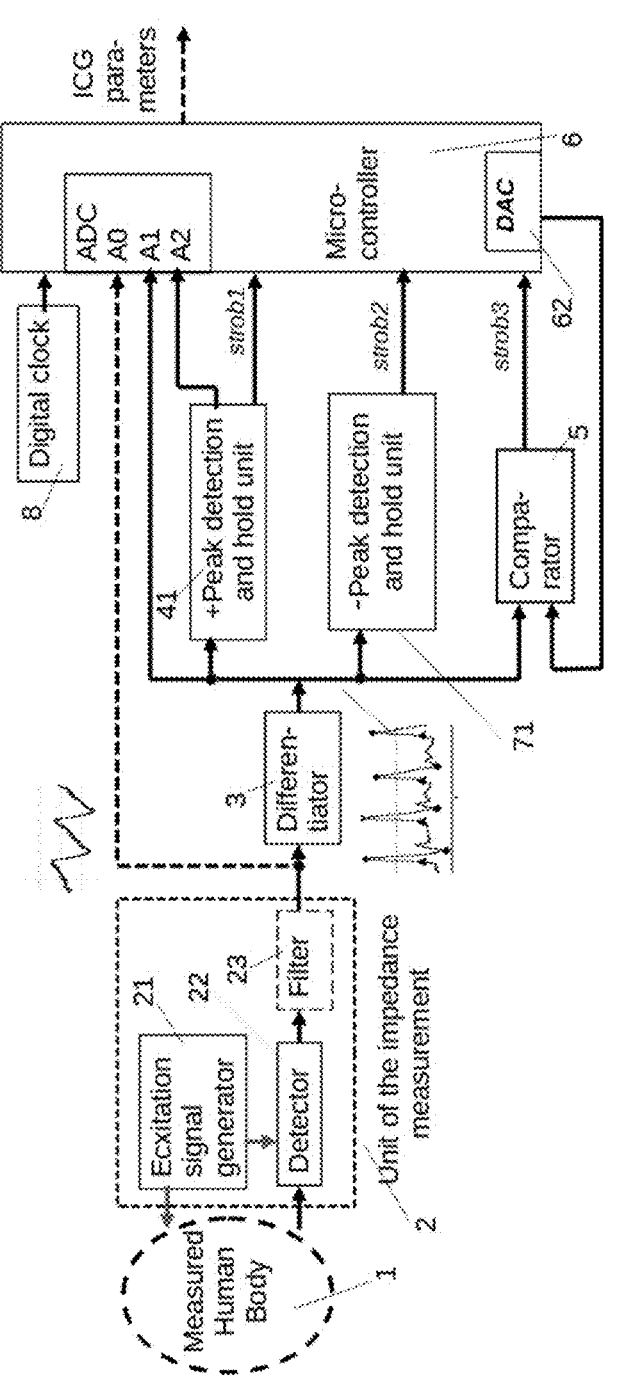
FIG. 6 shows the basic diagram of the device according to the invention, where the second input of the comparator 5 receives a signal from the output 61 of the digital-analog converter integrated with the microcontroller 6.

The solutions according to FIG. 5 and FIG. 6 differ in that the threshold for fixing point B (dZ/dt crossing from zero) is raised above the zero voltage (for example, to 15% of the amplitude value of point C), which is obtained in the case of FIG. 5 with a peak value with positive polarity from the hold output of the detection and hold unit 41 or, in the case of FIG. 6, generated by the digital-to-analog converter (DAC) 62 (performed, for example, by pulse-width modulation through a simple RC low-pass filter), integrated with the microcontroller 6.

Figure 7:
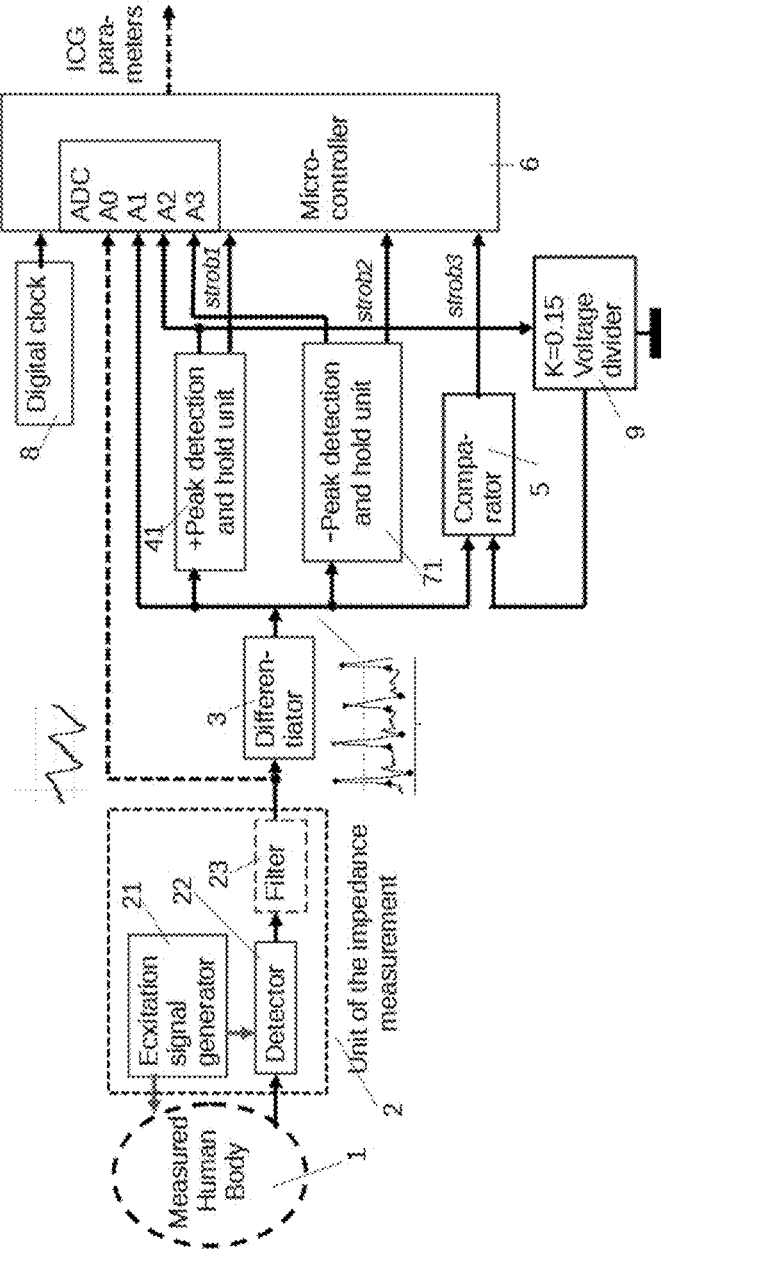
FIG. 7 shows the circuit diagram of the device according to the invention, where both positive and negative peak value detection units have, in addition to the strobing output, analog peak value hold outputs 41, 71, which are connected to the inputs of the analog-to-digital converter 61 integrated with the microcontroller 6.

The proposed solution according to FIG. 7 differs from the previously described solution in that both the positive and negative peak value detection units 4 and 7 contain also the functionality of fixing the corresponding analog peak values, and the positive peak value detection and hold unit 41 and the negative peak value detection and hold unit 71 send a fixed (hold) value to a separate input of the analog-to-digital converter. Such a solution allows the use of a significantly slower (eg integrative type) ADC 61, since the peak value detection unit works in this case as a fixed voltage holder, where the analog value is kept relatively constant for a longer time.

Figure 8:
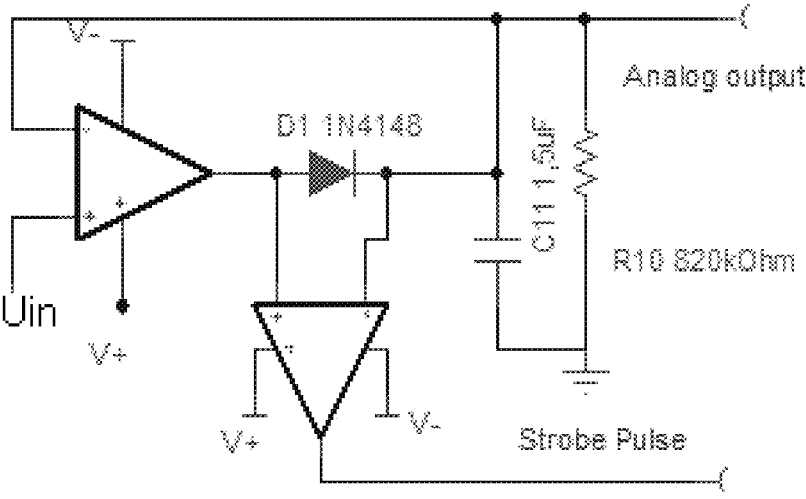
FIG. 8 shows the circuit diagram of a possible implementation example of the positive peak value detection unit 4 and the positive peak value detection and hold unit 41, together with the analog peak value hold output. For the negative peak value detection unit 7 and the negative peak value detection and hold unit 71, the polarity of the diode must be changed.

FIG. 8 shows an example of a possible implementation of the peak value detection unit. The circuit diagram includes an operational amplifier A1, non-inverting input of which is the input of the given unit, and negative feedback loop of it has a peak detector (D1, R1, C1). The voltage peak (maximum voltage value) is fixed on the capacitor C1. If the unit input voltage is less than the fixed peak value, the diode closes. Capacitor C1 holds a voltage that slowly decreases through resistor R1 (discharge rate depends on the time constant R1, C1).

FIG. 9 shows the measurement configurations for ICG signal acquisition. TEPC is from the chest 11 and AEPC is from the wrist 12a, 12b are examples of signals measured.

Figure 10:
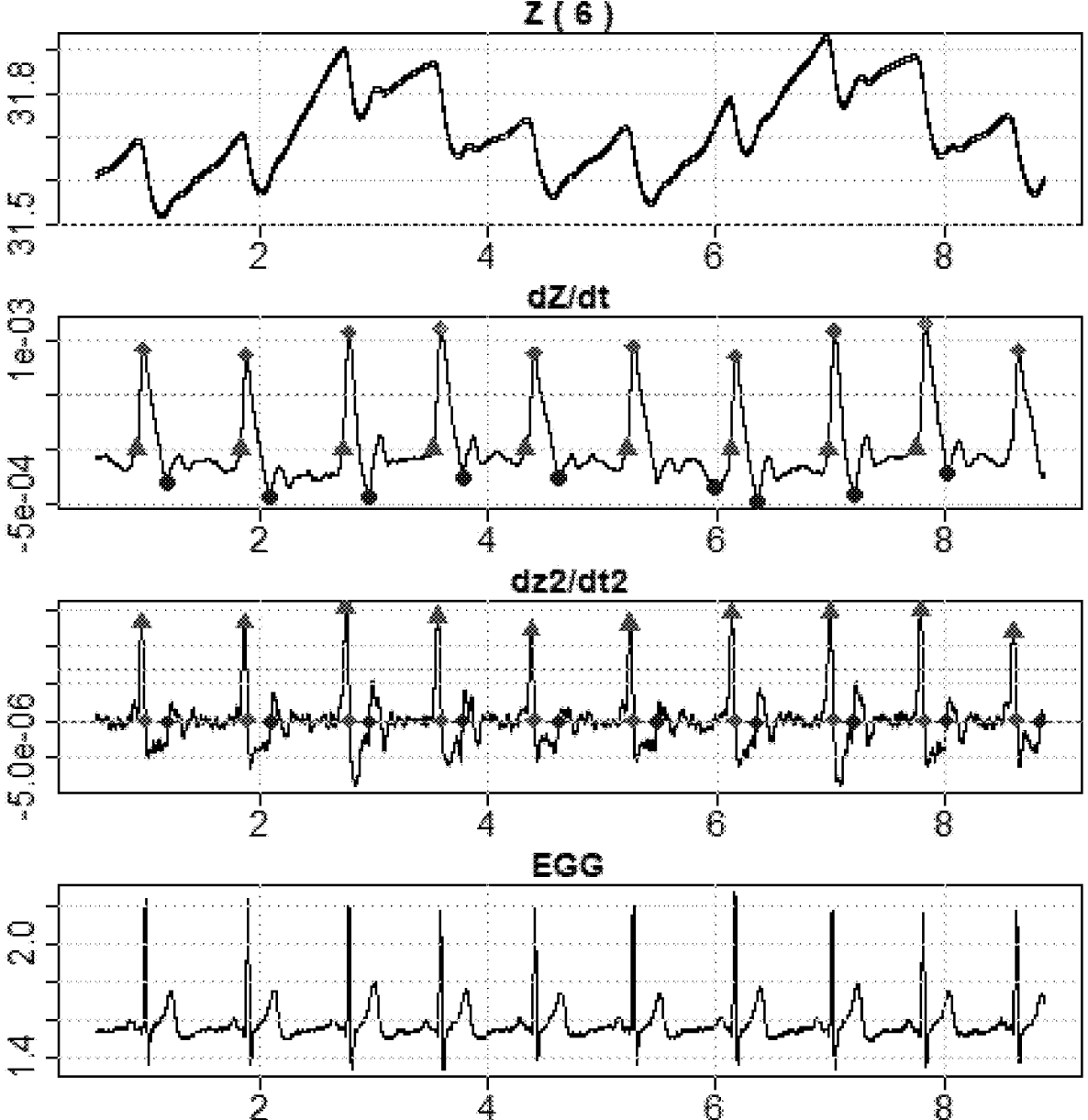
FIGS. 10 and 11 show examples of the impedance signals (from top to bottom, impedance Z, then the first derivative dZ/dt as the ICG signal, then the second derivative, which is used by a known solution, and then the ECG signal for the background), while in the case of FIG. 10, the signal comes from the chest (measurement configuration TEPC, FIG. 10) and in the case of FIG. 11 from the wrist (FIG. 11, AEPC).
Figure 11:
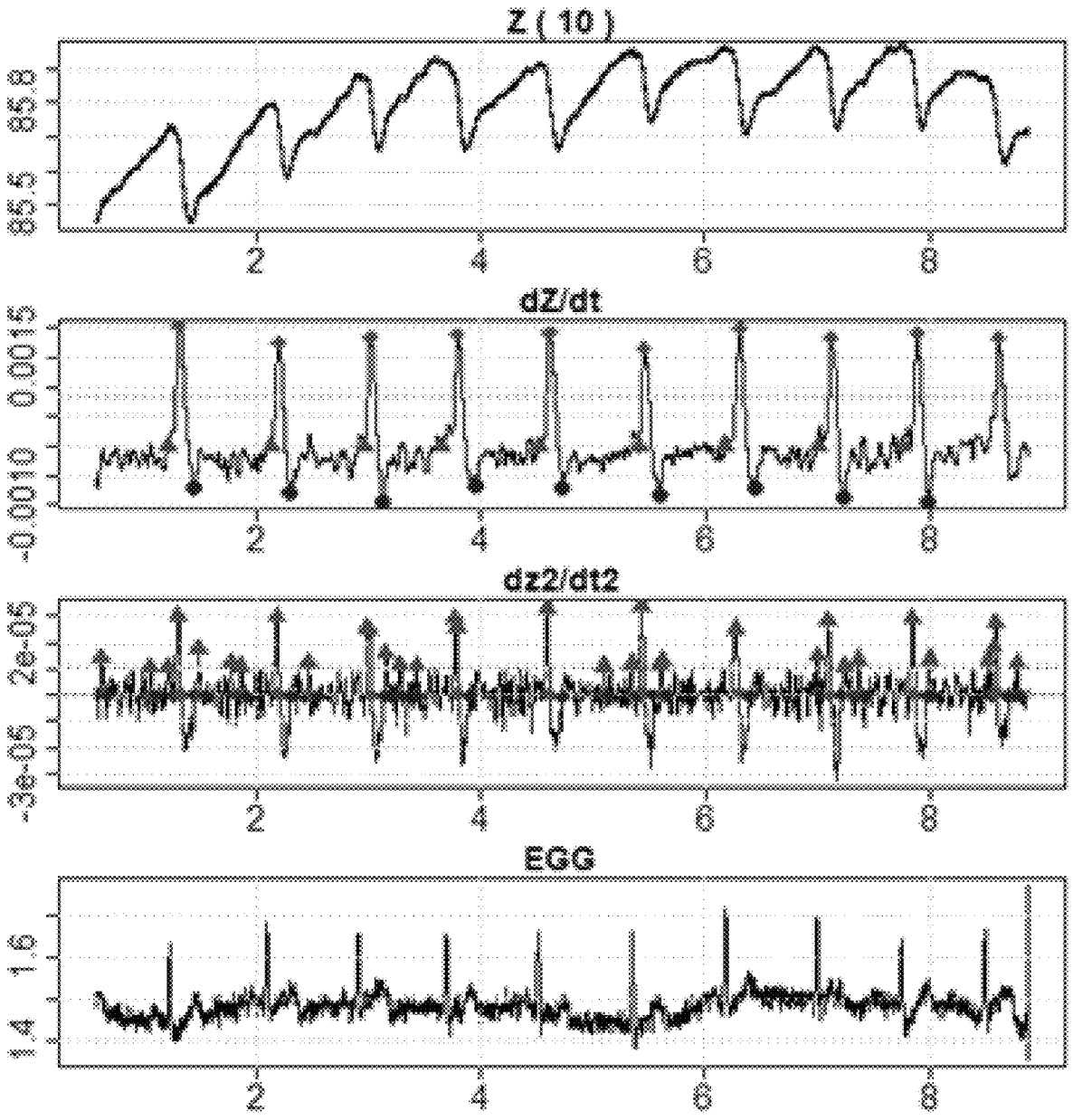

FIGS. 10 and 11 show examples of impedance signals (from top to bottom impedance Z, then the first derivative dZ/dt or ICG signal and the points B, X, C found by the proposed invention, then the second derivative used by the known solution, and then the ECG signal for background. In the case of FIG. 6, the signal originates from the chest (FIG. 5—measurement configuration TEPC) and in FIG. 7 from the wrist (FIG. 5—AEPC). The given results have been obtained by simulating the well-known solution proposed in this invention (U.S. Pat. No. 4,450,527) as electronic circuits, using real-life captured bioimpedance signals. A particularly large difference in the improvement of the accuracy of the detection of ICG points (compared to the known solution) is in the case of the (relatively small amplitude) signal received from the wrist.

The invention claimed is:

1. An impedance cardiography device, comprising an impedance measurement unit (2) configured to be connected to the human body (1) to be measured, a differentiator (3), a comparator (5) and a microcontroller (6) integrated with an analog-to-digital converter (61), wherein the impedance measurement unit (2) the output is connected to the input of the differentiator (3), the output of which is connected to the input of the analog-to-digital converter (61) integrated with the microcontroller (6) and through the comparator (5) to the first binary input of the microcontroller, wherein the device comprises a positive polarity peak value signal detection unit (4) and a negative polarity peak value detection unit (7), whose binary outputs are connected to the second and third binary inputs of the microcontroller (6), respectively.

2. The impedance cardiography device according to claim 1, wherein the unit for detecting the positive polarity peak value (4) comprises the unit (41) for holding the analog value of the positive peak value, whereby the analog output for holding the peak value of this unit is connected to the microcontroller (6) integrated analog- to the second input of the digital converter (61).

3. The impedance cardiography device according to claim 2, wherein the second input of the comparator (5) is connected through the voltage divider (9) to the analog hold output of unit (41) for detecting and holding the positive peak value.

4. The impedance cardiography device according to claim 3, wherein the transfer coefficient of said voltage divider (9) is 0.15.

5. The impedance cardiography device according to claim 2, wherein the second input of the comparator (5) is connected to the output of the digital-to-analog converter (62) integrated with the microcontroller (6).

6. The impedance cardiography device according to claim 2, wherein said positive peak value detection unit (4), negative peak value detection unit (7), positive peak value detection and hold unit (41) and negative peak value detection and hold unit (71) consist of an operational amplifier, a comparator, a diode, a capacitor and a resistor, with the non-inverting input of the operational amplifier connected to the input of the given unit, the output through a (semiconductor) diode to the inverting input of the same operational amplifier, which in turn is connected to ground through the parallel connection of the resistor and capacitor, and the first input of the comparator is connected with one terminal of the diode and the other input with the other terminal of the diode and the output of the comparator is the binary output of the unit.

7. The impedance cardiography device according to claim 6, wherein said positive peak value detection unit (4) and negative peak value detection unit (7) contain an analog peak value hold output connected to the inverting input of the operational amplifier.

8. The impedance cardiography device according to claim 1, wherein the units for detecting the peak value of positive and negative polarity signals are also units (41, 71) for holding the analog value of the peak value, wherein the analog outputs of the hold values of the peak value of positive and negative polarity are connected to the second and third inputs respectively of the analog-to-digital converter (61) integrated with the microcontroller (6).

* * * * *